US009757158B2

(12) United States Patent
Fessler

(10) Patent No.: US 9,757,158 B2
(45) Date of Patent: Sep. 12, 2017

(54) MINIMALLY INVASIVE SPINAL COLUMN REALIGNMENT SYSTEM AND METHOD

(71) Applicant: IN QUEUE INNOVATIONS, LLC, Winona Lake, IN (US)

(72) Inventor: Richard G. Fessler, Winnetka, IL (US)

(73) Assignee: IN QUEUE INNOVATIONS, LLC, Winona Lake, IN (US)

( * ) Notice: Subject to any disclaimer, the term of this patent is extended or adjusted under 35 U.S.C. 154(b) by 32 days.

(21) Appl. No.: 14/649,943

(22) PCT Filed: Dec. 6, 2013

(86) PCT No.: PCT/US2013/073634
§ 371 (c)(1),
(2) Date: Jun. 5, 2015

(87) PCT Pub. No.: WO2014/089467
PCT Pub. Date: Jun. 12, 2014

(65) Prior Publication Data
US 2015/0313642 A1    Nov. 5, 2015

Related U.S. Application Data

(60) Provisional application No. 61/734,189, filed on Dec. 6, 2012.

(51) Int. Cl.
*A61B 17/70* (2006.01)
(52) U.S. Cl.
CPC ........ *A61B 17/7014* (2013.01); *A61B 17/701* (2013.01); *A61B 17/7032* (2013.01); *A61B 17/7079* (2013.01)

(58) Field of Classification Search
CPC ............ A61B 17/7074; A61B 17/7079; A61B 17/7014; A61B 17/7083; A61B 17/7085; A61B 17/7089
See application file for complete search history.

(56) References Cited

U.S. PATENT DOCUMENTS 5,620,443 A    4/1997  Gertzbein et al.
7,618,444 B2   11/2009 Shluzas
(Continued)

OTHER PUBLICATIONS

Jun. 9, 2015: International Preliminary Report on Patentability in International Patent Application No. PCT/US2013/073634.
(Continued)

*Primary Examiner* — Julianna N Harvey
(74) *Attorney, Agent, or Firm* — Heslin Rothenberg Farley & Mesiti P.C.; John W. Boger

(57) ABSTRACT

The present invention discloses a minimally invasive spinal column realignment system and method of use. The spinal column realignment system includes at least two fasteners, a member, an outer sleeve, an inner sleeve, and an instrument. The at least two fasteners are configured for insertion into two adjacent vertebral bodies of a patient. The member is configured to engage the at least two fasteners. The outer sleeve includes a first opening and a second opening and the inner sleeve is configured for insertion through the first opening of the outer sleeve to engage a first fastener of the at least two fasteners and the member. The instrument is configured for insertion through the second opening in the outer sleeve and engagement with the member. A method of using a spinal column realignment system is also disclosed.

20 Claims, 14 Drawing Sheets

(56) References Cited

U.S. PATENT DOCUMENTS

| | | | |
|---|---|---|---|
| 2008/0077138 A1* | 3/2008 | Cohen | A61B 17/708 |
| | | | 606/86 A |
| 2010/0049206 A1* | 2/2010 | Biyani | A61B 17/7002 |
| | | | 606/104 |
| 2011/0307013 A1 | 12/2011 | Winslow et al. | |
| 2012/0130429 A1* | 5/2012 | Mitchell | A61B 17/7004 |
| | | | 606/259 |
| 2012/0253400 A1 | 10/2012 | Clark et al. | |
| 2012/0303062 A1 | 11/2012 | Amstutz et al. | |
| 2014/0128930 A1* | 5/2014 | Meyer | A61B 17/7083 |
| | | | 606/86 A |

OTHER PUBLICATIONS

International Search Report for PCT/US2013/073634 dated Mar. 6, 2014.

* cited by examiner

MINIMALLY INVASIVE SPINAL COLUMN REALIGNMENT SYSTEM AND METHOD

CROSS REFERENCE TO RELATED APPLICATIONS

This application is a national stage filing under section 371 of International Application No. PCT/US2013/073634 filed on Dec. 6, 2013, and published in English on Jun. 12, 2014as WO 2014/089467 A1 and claims priority benefit under 35 U.S.C. §119(e) of U.S. provisional patent application No. 61/734,189 on Dec. 6, 2012, which is incorporated herein by reference in their entirety.

FIELD OF THE INVENTION

The present invention relates generally to general surgery, orthopaedic and neurosurgical implants used for insertion within a patient's vertebrae. More specifically, but not exclusively, the present invention concerns a minimally invasive realignment system implanted in the spine to maintain or re-establish proper spacing and alignment within a patient's spine.

BACKGROUND OF THE INVENTION

One example of a spinal deformity is spondylolisthesis which is a sagittal plane deformity in which one vertebral body dislocates or slips forward on the vertebral body immediately adjacent to it. Ideal correction of spondylolisthesis requires both reduction and translation. Minimally invasive surgical techniques have made it possible to achieve reduction of spondylolisthesis, but not translation. The only available option for achieving translation has been using an open surgical technique. In addition, the available options for minimally invasive surgical techniques only allow correction of grade I or II slips.

SUMMARY OF THE INVENTION

Aspects of the present invention provide a minimally invasive realignment system and method that can maintain or re-establish anatomic spacing within a patient's spine.

In one aspect, provided herein is a spinal column realignment system, including at least two fasteners for insertion into two adjacent vertebral bodies of a patient and a member for engaging the at least two fasteners. The system may also include an outer sleeve including a first opening and a second opening. The system may further include an inner sleeve for insertion through the first opening of the outer sleeve to engage a first fastener of the at least two fasteners and the member. Further, the system may include an instrument configured for insertion through the second opening and engagement with the member.

In another aspect, provided herein is a method for using a realignment system including creating an incision in a patient over a dislocated vertebra. The method also includes inserting a screw assembly into the dislocated vertebra. The screw assembly includes a first fastener, an inner sleeve, and an outer sleeve. The method further includes inserting a second fastener into an adjacent vertebral body. The method may further include sliding a member into the incision to engage the screw assembly and the second fastener. Next the method may include securing the member to the second fastener. The method may also include attaching a realignment tool to the screw assembly. The method may include moving the realignment tool to provide for movement of the dislocated vertebra in an anterior or posterior direction. The method may further include inserting an instrument through the outer sleeve, wherein the instrument engages a plurality of slots on the member, and rotating the instrument to provide movement of the dislocated vertebra relative to the adjacent vertebral body in an inferior-superior direction. Next, the method may include achieving a desired anterior-posterior position and inferior-superior position for the dislocated vertebra and securing the member in the first fastener. The method may finally include removing the instrument, the outer sleeve, and the inner sleeve from the patient and closing the patient's incision. These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention.

DETAILED DESCRIPTION FOR CARRYING OUT THE INVENTION

Generally stated, disclosed herein is a minimally invasive realignment system. Further, a surgical method for inserting the minimally invasive realignment system is discussed.

In this detailed description and the following claims, the words proximal, distal, anterior, posterior, medial, lateral, superior, inferior, cephalad and caudally are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure, "cephalad" means a direction toward the head and "caudally" means a direction toward the inferior part of the body.

Figure 1:
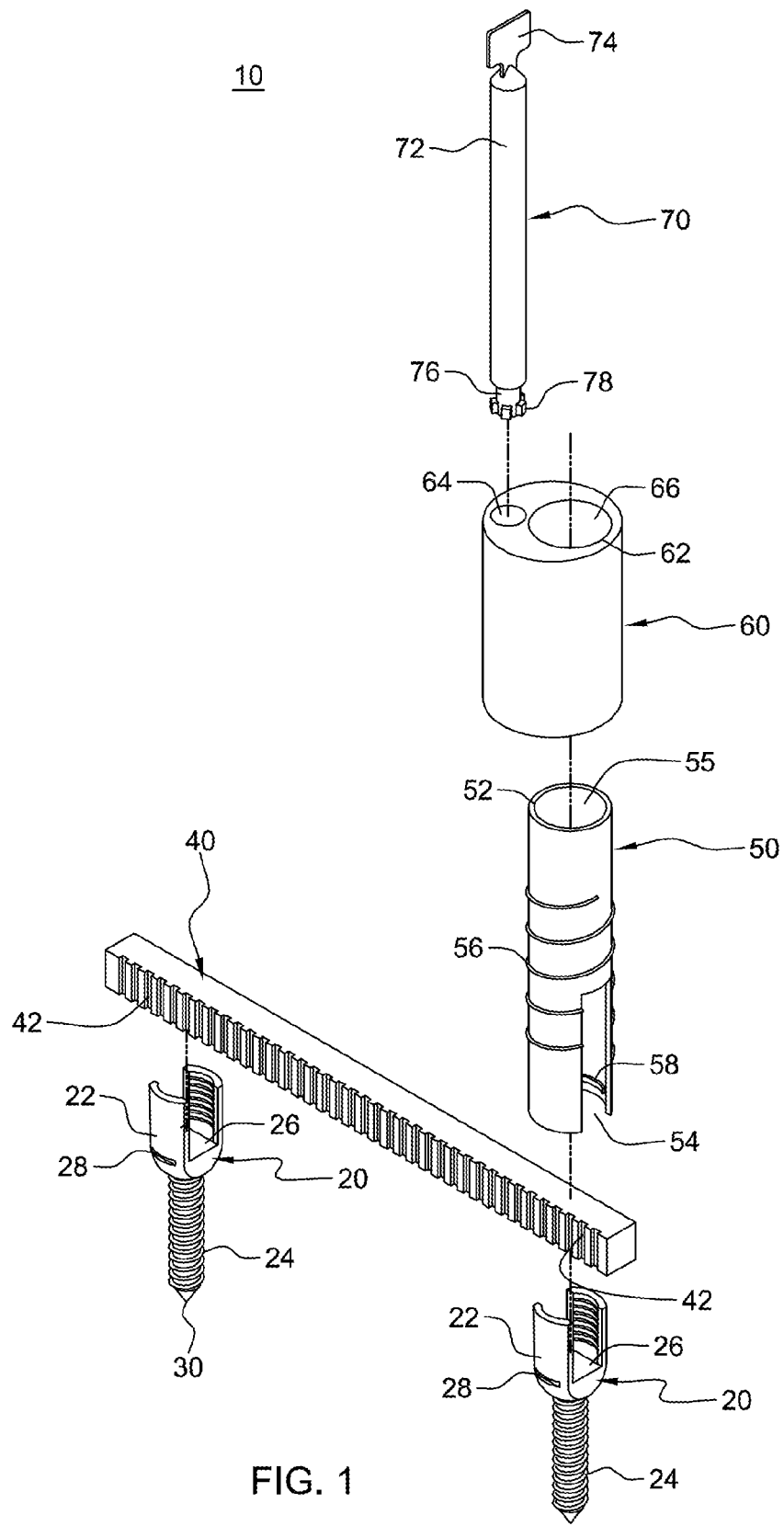
FIG. 1 is an exploded view of the minimally invasive realignment system, in accordance with an aspect of the present invention.
Figure 2:
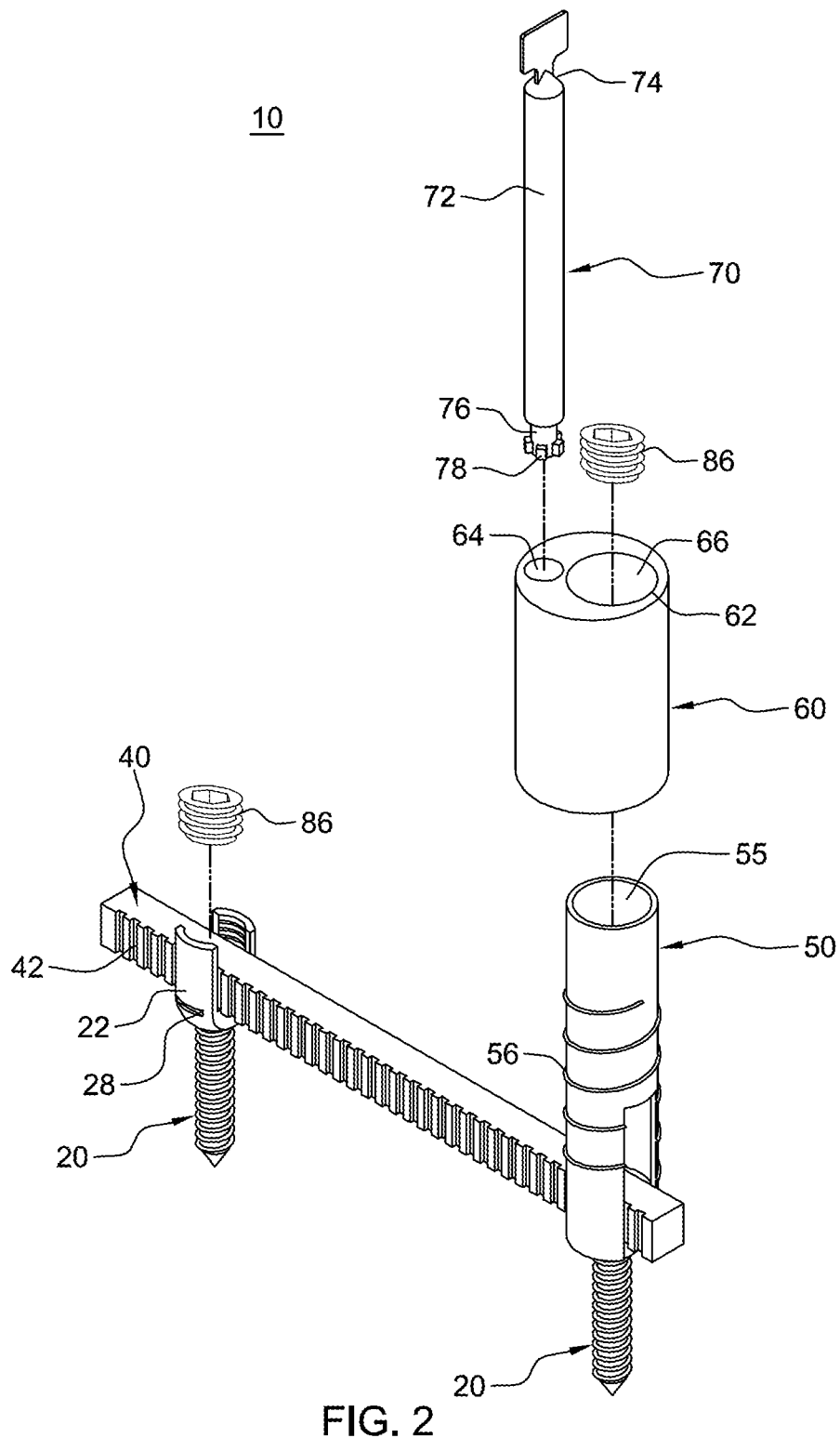
FIG. 2 is a partially exploded view of the minimally invasive realignment system of FIG. 1, in accordance with an aspect of the present invention.
Figure 3:
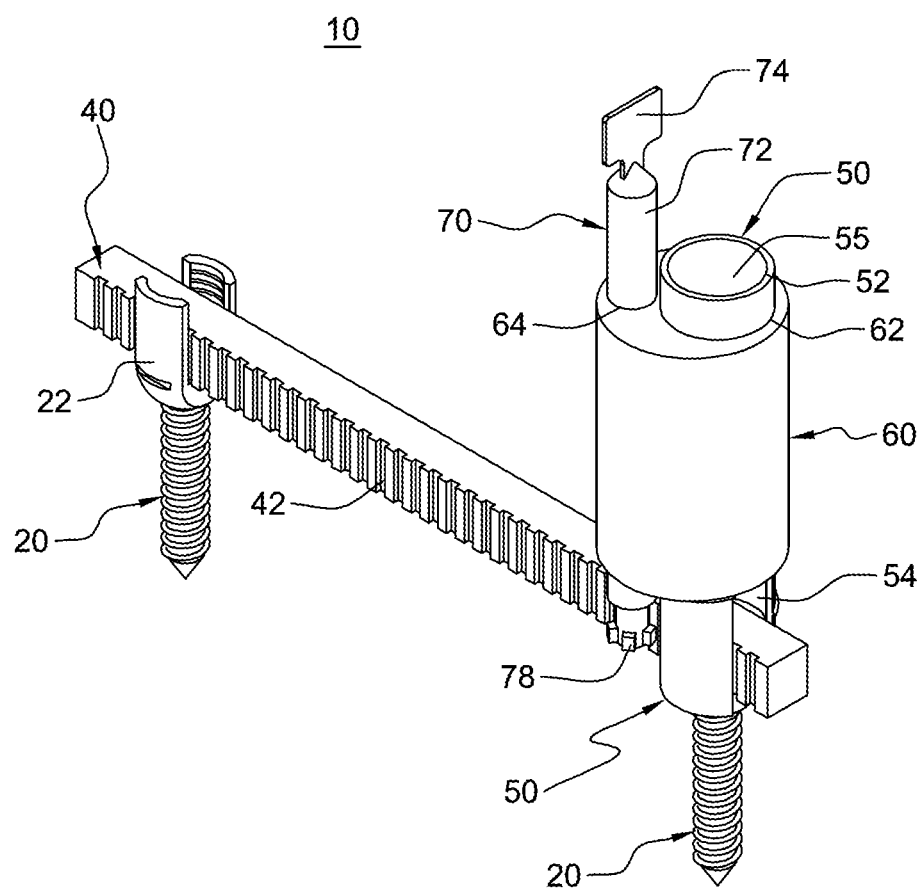
FIG. 3 is a perspective view of the minimally invasive realignment system of FIG. 1, in accordance with an aspect of the present invention.
Figure 4:
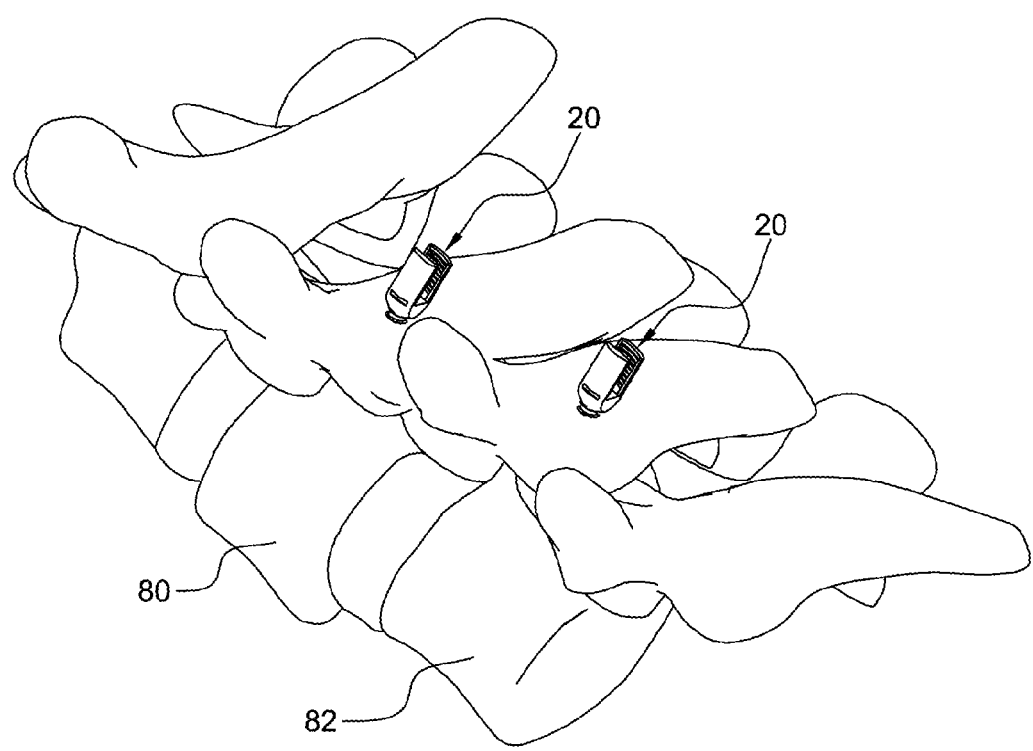
FIG. 4 is lateral perspective view of a portion of a patient's spine showing the position of the two fasteners of the minimally invasive realignment system of FIG. 1 inserted into two adjacent vertebrae, in accordance with an aspect of the present invention.

Referring to the drawings, wherein like reference numerals are used to indicate like or analogous components throughout the several views, and with particular reference to FIGS. 1-3, there is illustrated an exemplary embodiment of a minimally invasive realignment system or spinal column realignment system 10. The system 10 may likely include at least two fasteners 20, a ratcheting bar or member 40, an alignment assembly that may include an inner sleeve 50, an outer sleeve 60, and a ratcheting instrument or instrument 70. The system 10 may also include at least two set screws or locking caps 86. The fasteners 20 may be, for example, pedicle screws which include a head 22 and a threaded shank 24. The pedicle screws may, for example, be fixed or polyaxial. The head 22 of the fasteners 20 may include an inner channel 26 through the head 22 of the fasteners 20. The exterior surface of each head 22 includes at least one groove or slot 28 for engaging the inner sleeve 50. The shank 24 extends distally from the head 22 of the fasteners 20 and may include an end 30 configured to assist in insertion into the spine or bone.

The ratcheting bar 40 may engage the inner channels 26 of the fastener heads 22 to facilitate the spacing between two adjacent vertebrae. The ratcheting bar 40 may have, for example, a generally rectangular shape with, for example, a square cross-section and one lateral side of the ratcheting bar 40 may include a plurality of slots 42. The cross-section shape of the bar 40 may also include, but not be limited to a circular, round, oval or polygonal shape and may include circumferential flanges to engage the ratcheting instrument 70. The plurality of slots 42 of the ratcheting bar 40 are sized to mate with the protrusions 78 of the instrument head 76. Alternative arrangements for the plurality of slots 42 on the ratcheting bar 40 are also contemplated, for example, the ratcheting bar 40 may contain a plurality of slots 42 on half of the ratcheting bar 40 or only on the portion of the ratcheting bar 40 that may mate with the instrument 70.

As shown in FIG. 2, the alignment assembly may include an inner sleeve 50 that fits over the ratcheting bar 40 following insertion of the ratcheting bar 40 into the fastener 20 and engages the at least one groove 28 on the fastener 20. The inner sleeve 50 may include a center opening 52 with a passageway or lumen 55 through the center and a channel or opening 54 on the distal end of the inner sleeve 50 which may be perpendicular to passageway 55 for engaging a fastener 20 and allowing the ratcheting bar 40 to pass through.

The channel 54 may include a protrusion 58 (see FIG. 1) on the inner surface of the inner sleeve 50 for engaging the groove 28 in the fastener 20 as the inner sleeve 50 is inserted over the fastener 20. The inner sleeve 50 may also include a thread 56 disposed on the exterior surface of the inner sleeve 50. The thread 56 on the exterior surface of the inner sleeve 50 may engage an inner surface 66 of the outer sleeve 60. The inner sleeve 50 may be used for movement of the cephalad vertebra which has dislocated or slipped out of alignment in the patient's spine.

Referring now to FIG. 3, the outer sleeve 60 may include a first opening 62 and a second opening 64 passing through the interior of the outer sleeve 60. The inner surface 66 may include a corresponding groove or channel that may mate with the thread 56 on the inner sleeve 50 when the outer sleeve 60 is inserted over the inner sleeve 50. The second opening 64 allows for the instrument 70 to pass through the second opening 64 to engage the ratcheting bar 40. The instrument 70 may include a shaft 72 with a handle 74 on a superior end of the shaft 72 and a head 76 including protrusions 78 for engaging the plurality of slots 42 on the ratcheting bar 40 on an inferior end of the shaft 72.

The at least two set screws or locking caps 86 may be used for locking the ratcheting bar 40 in a desired position within the two fasteners 20. The realignment system 10 may be inserted into a patient using minimally invasive spine ("MIS") surgical techniques to allow a surgeon to reduce and/or translate a patient's vertebrae. Referring now to FIGS. 4-9, a method of using the minimally invasive realignment system 10 is shown. The method of inserting the system 10 may occur before or after a release and fusion surgical procedure is performed by the surgeon. An exemplary method of inserting the system 10 may include preparing the spine for insertion of the fasteners 20 into the positions shown in FIG. 4, by for example, using anterior-posterior fluoroscopy to insert K-wires into the pedicles through Jamshidi needles using a bulls-eye technique. The use of other known K-wires insertion methods is also contemplated. Once the K-wires are confirmed to be within the pedicles, the fluoroscope may then be moved to a lateral position and the K-wires may be advanced through the pedicles into the vertebral bodies 80, 82. After the K-wires are inserted into the vertebral bodies 80, 82, a series of dilators may then be passed over the K-wires and tapping may be performed through the largest dilator. The dilators may then be removed and a screw assembly 84 may be passed over the K-wire into the pedicle and the vertebral body 80 and a screw assembly 84 or 92 may be passed over the K-wire into the pedicle and the vertebral body 82.

The screw assembly 84 may include a fastener 20, inner sleeve 50, and outer sleeve 60. The fastener 20 may, for example, be a pedicle screw. Prior to insertion into the patient, the fastener 20, inner sleeve 50, and outer sleeve 60 may be assembled to create the screw assembly 84. The screw assembly 84 is created by inserting a fastener 20 into the inner sleeve 50. The fastener 20 is inserted into the channel 54 of the inner sleeve 50. Once the fastener 20 is completely inside the channel 54, the fastener 20 may be turned and the at least one protrusion 58 on the inner wall of the channel 54 of the inner sleeve 50 may engage the at least one groove 28 on the fastener to secure the fastener 20 to the inner sleeve 50.

Alternative arrangements for securing the fastener 20 to the inner sleeve 50 of the screw assembly 84 are also contemplated, for example the fastener 20 may be secured to the inner sleeve 50 with a detent mechanism or like temporary securement mechanism. Then the outer sleeve 60 may be slid over the inner sleeve 50 by inserting the inner sleeve 50 into the first opening 62 of the outer sleeve 60. The first opening 62 of the outer sleeve 60 may include a groove or threads to engage the thread 56 on the exterior of the inner sleeve 50. The screw assembly 92 may include a fastener 20, inner sleeve 50, and outer sleeve 90. The fastener 20 may, for example, be a pedicle screw. Prior to insertion into the patient, the fastener 20, inner sleeve 50, and outer sleeve 90 may be assembled to create the screw assembly 92, which may be assembled as described above with reference to the assembly of screw assembly 84.

Figure 5:
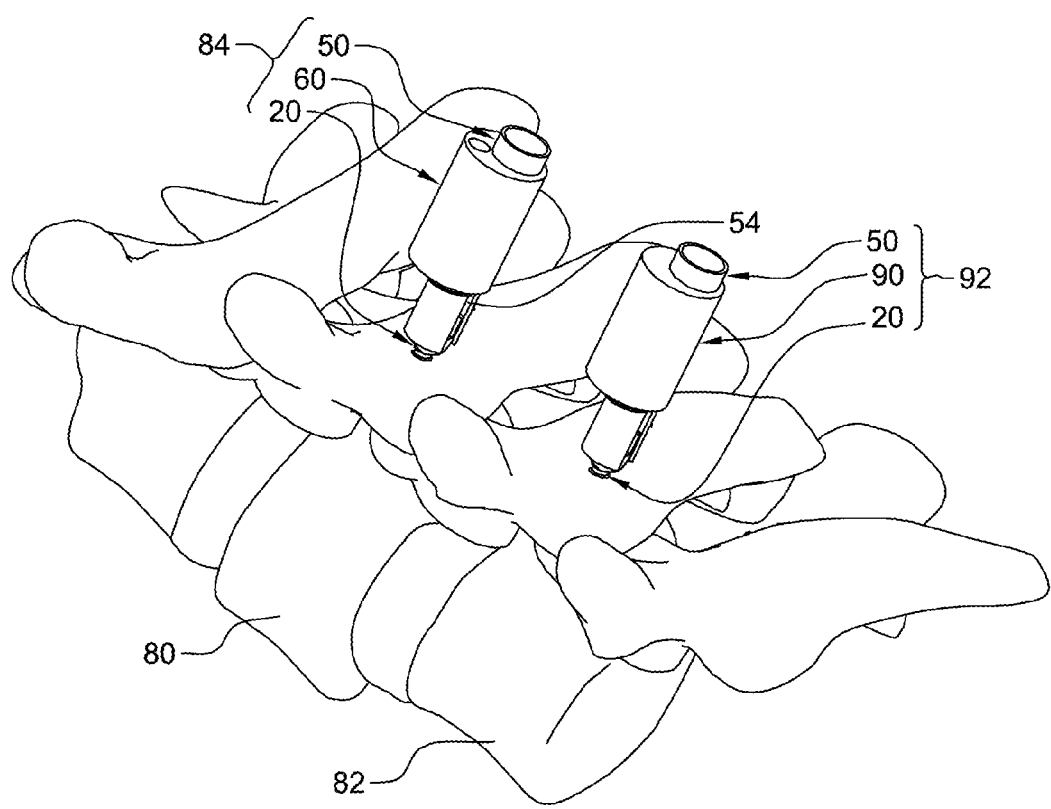
FIG. 5 is a lateral perspective view of the patient's spine of FIG. 4 showing an alignment assembly of the minimally invasive realignment system inserted into the patients spine, in accordance with an aspect of the present invention.

Once the screw assemblies 84, 92 are assembled and inserted into the pedicle and vertebral body 80, the K-wire may be removed. The screw assembly 84 may be inserted into a cephalad vertebral body 80, which may be dislocated, and the screw assembly 92 may be inserted into a caudal vertebral body 82, as shown in FIG. 5. The fastener insertion process, described above, may alternatively be used to insert a second screw assembly 84 into a caudal vertebral body 82 adjacent to the cephalad vertebral body 80. Alternatively, a currently available fastener insertion system may be used to insert and hold the fastener 20 in the caudal vertebral body 82. The realignment system 10 is used on the fastener 20 inserted into the cephalad vertebral body or dislocated vertebra 80 to not only hold the fastener 20 in place, but also contains an opening 64 through which the instrument 70 may be inserted to engage the ratcheting bar 40.

Figure 6:
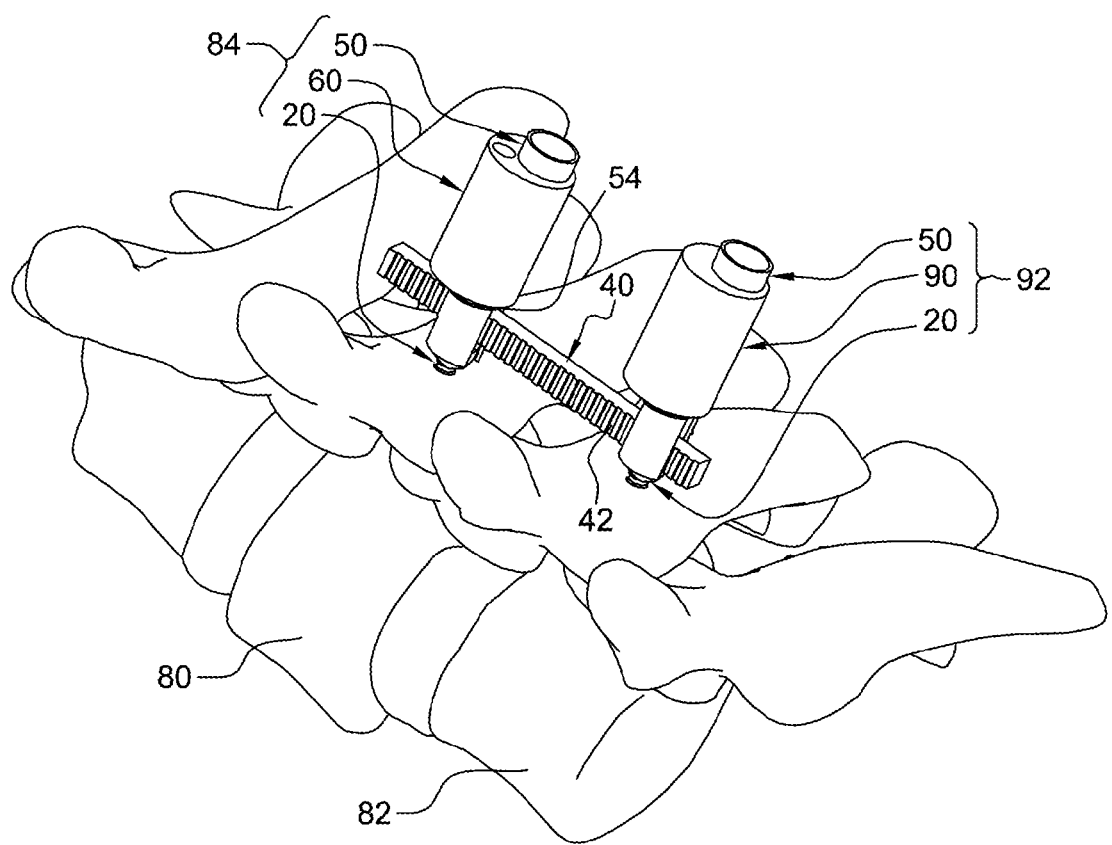
FIG. 6 is a lateral perspective view of the patient's spine of FIG. 4 also showing a ratcheting bar of the minimally invasive realignment system engaging the two fasteners of FIG. 5, in accordance with an aspect of the present invention.
Figure 7:
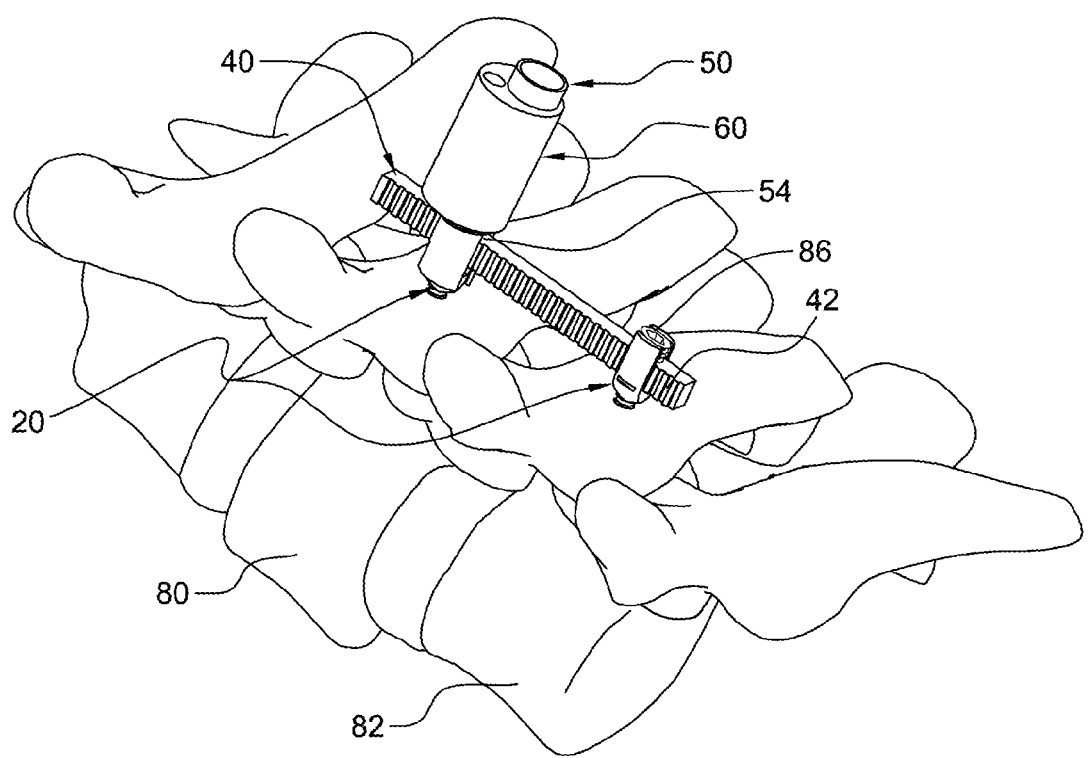
FIG. 7 is a lateral perspective view of the patient's spine in FIG. 4 also showing the ratcheting bar of the minimally invasive realignment system secured into the second fastener, in accordance with an aspect of the present invention.

After the fasteners 20 are inserted into the vertebral bodies 80, 82, the next the ratcheting bar or member 40 may slide into the screw assembly 84 inserted in the cephalad vertebral body 80 and the screw assembly 92 inserted in the caudal vertebral body 82. The ratcheting bar 40 may, for example, be inserted first through the cephalad screw assembly 84 and then through the caudal screw assembly 92. Alternatively, the ratcheting bar 40 may, for example, be inserted first through the caudal screw assembly 92 and then passed through the cephalad screw assembly 84. The ratcheting bar 40 may pass through the screw assembly 92 by passing through an opening created by the head 22 of the fastener 20 in the caudal vertebral body 82 and the channel 54 of the inner sleeve 50, as shown in FIG. 6. The ratcheting bar 40 may also pass through the screw assembly 84 by passing through an opening created by the head 22 of the fastener 20 in the cephalad vertebral body 80 and the channel 54 of the inner sleeve 50, also shown in FIG. 6. Once a desired position of the ratcheting bar 40 is achieved, a set screw or locking cap 86 may be inserted into the fastener 20 in the caudal vertebral body 82, as shown in FIG. 7. The set screw or locking cap 86 may then be passed through the inner sleeve 50 of the screw assembly 92 to engage the inner channel 26 of the fastener 20 in the caudal vertebral body 82. The set screw or locking cap 86 may be inserted to secure the ratcheting bar 40 in the desired position within the head 22 of the fastener 20 in the caudal vertebral body 82. For illustrative purposes, the screw assembly 92 has been removed from FIGS. 7 and 8, however, in the described method the screw assembly 92 may still remain in the patient until the desired reduction and translation is achieved.

Figure 8:
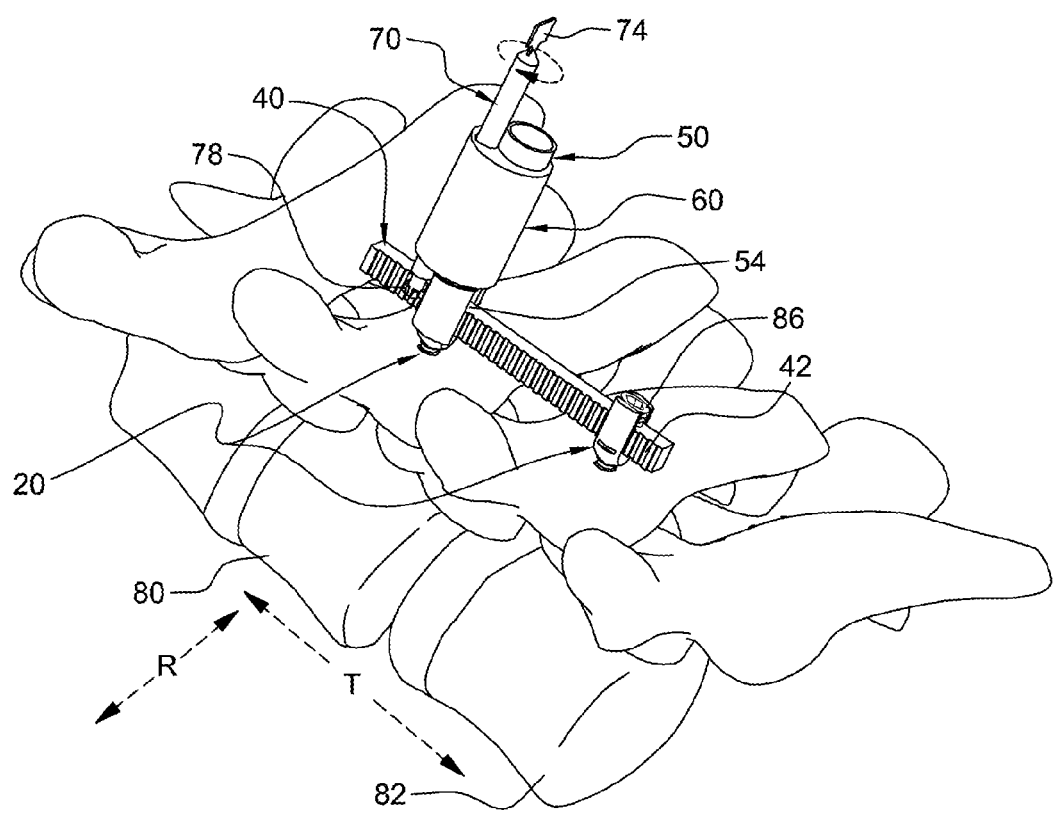
FIG. 8 is a lateral perspective view of the patient's spine of FIG. 4 also showing a ratcheting instrument of the minimally invasive realignment system inserted into the outer sleeve of the alignment assembly and engaging the ratchet bar of FIG. 7, in accordance with an aspect of the present invention.
Figure 14:
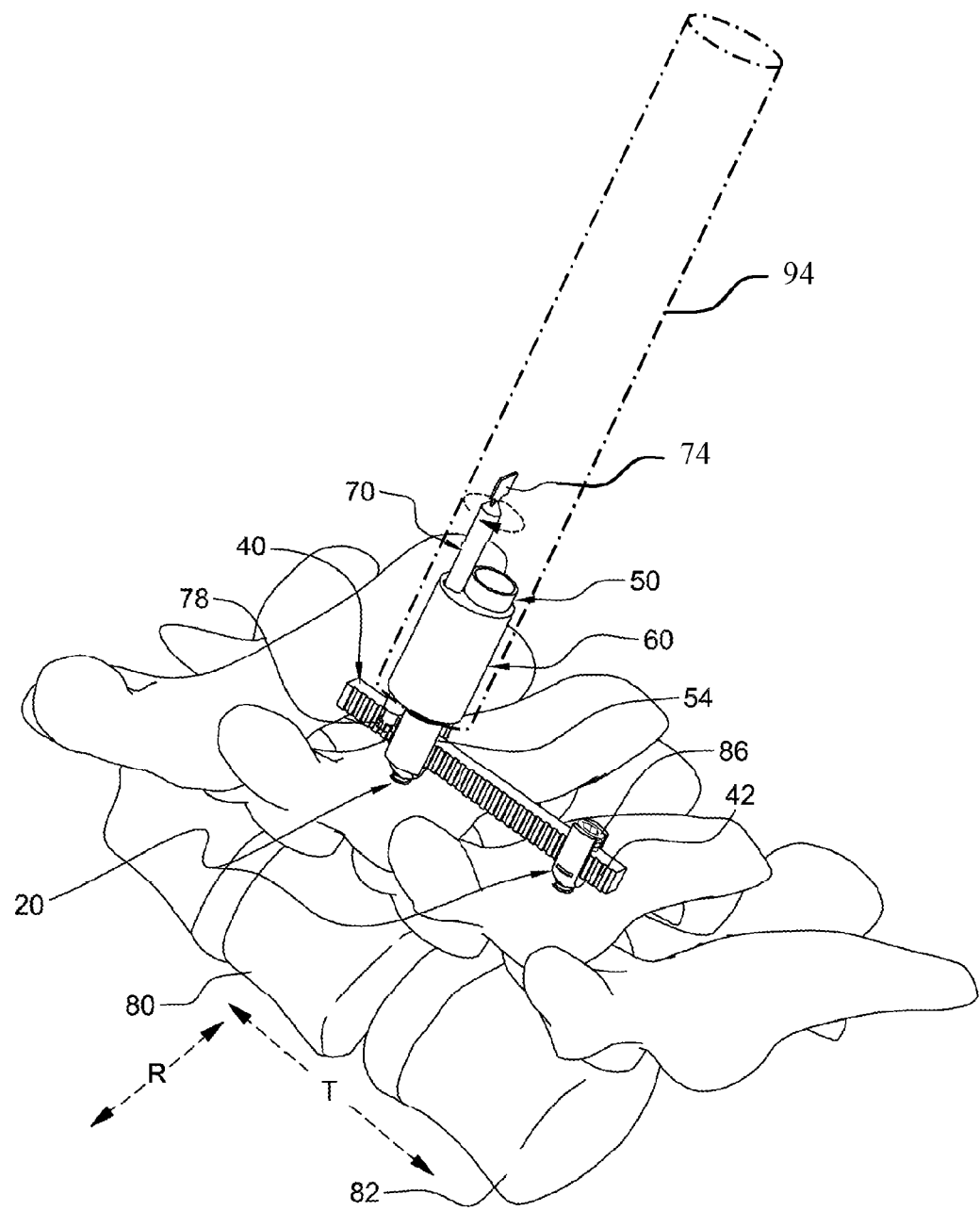
FIG. 14 is a lateral perspective view of the patient's spine of FIG. 8 also showing an alignment tool coupled to the outer sleeve of FIG. 8, in accordance with an aspect of the present invention.

As shown in FIG. 14, a realignment tool 94 may then be locked or secured to the outer sleeves 60 of the screw assemblies 84, 92 to perform the reduction or facilitate the manipulation of the dislocated vertebra 80. Alternatively, the realignment tool 94 may be secured to both the inner sleeve 50 and the outer sleeve 60 of screw assembly 84 to enable movement of the outer sleeve 60 with respect to the inner sleeve 50 to reduce the dislocated vertebra 80. The realignment tool 94 is configured to be secured to a portion of the screw assembly 84 to facilitate anterior-posterior movement of the cephalad vertebral body 80. Once the realignment tool 94 is secured to the realignment system 10, the surgeon may begin to pull the cephalad vertebral body 80 posteriorly (or anteriorly, if required) and back into alignment with the rest of the spinal column. As the surgeon begins reducing of the dislocated vertebra 80, he may insert the instrument 70 into the second opening 64 of the outer sleeve 60. As the instrument 70 is inserted into the outer sleeve 60, the protrusions 78 on the head 76 of the instrument 70 engage the plurality of slots 42 on the ratcheting bar 40. As reduction of the dislocated vertebra 80 is occurring, the instrument 70 may be turned to cause the member 40 to translate causing the dislocated vertebra 80 to move in an inferior-superior direction relative to the caudal vertebral body 82. As shown in FIG. 8, the realignment tool 94 and instrument 70 may be used simultaneously to reduce (R) and translate (T) the dislocated vertebra 80 relative to the caudal vertebral body 82. As the dislocated vertebra 80 is reduced, the ratcheting bar 40 moves farther down the channel 54 of the inner sleeve 50 until it reaches the head 22 of the fastener 20 in the dislocated vertebra 80, as seen in FIG. 8.

Once a desired amount of reduction and translation of the cephalad vertebral body 80 is achieved to realign the patient's spinal column, then a set screw or locking cap 86 may be inserted into the head 22 of the fastener 20 through the opening 52 in the inner sleeve 50 to secure the ratcheting bar 40 in the desired position within the head 22 of the fastener 20 in the cephalad vertebral body 80. After the ratcheting bar 40 is secured to the fasteners 20, the instrument 70, outer sleeve 60 and inner sleeve 50 may be removed from the cephalad vertebral body 80. The screw assembly used to insert the fastener 20 into the caudal vertebral body 82 may also be removed.

Figure 9:
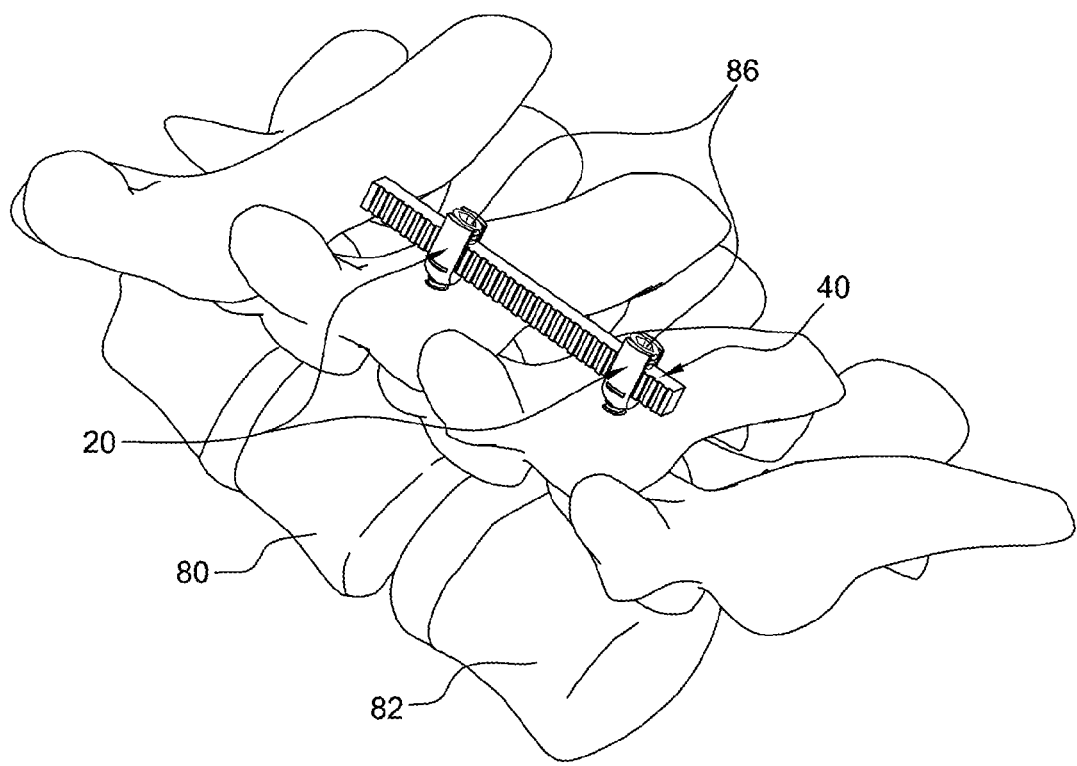
FIG. 9 is a lateral perspective view of the patient's spine of FIG. 4 after reduction and translation by the minimally invasive realignment system, in accordance with an aspect of the present invention.
Figure 13:
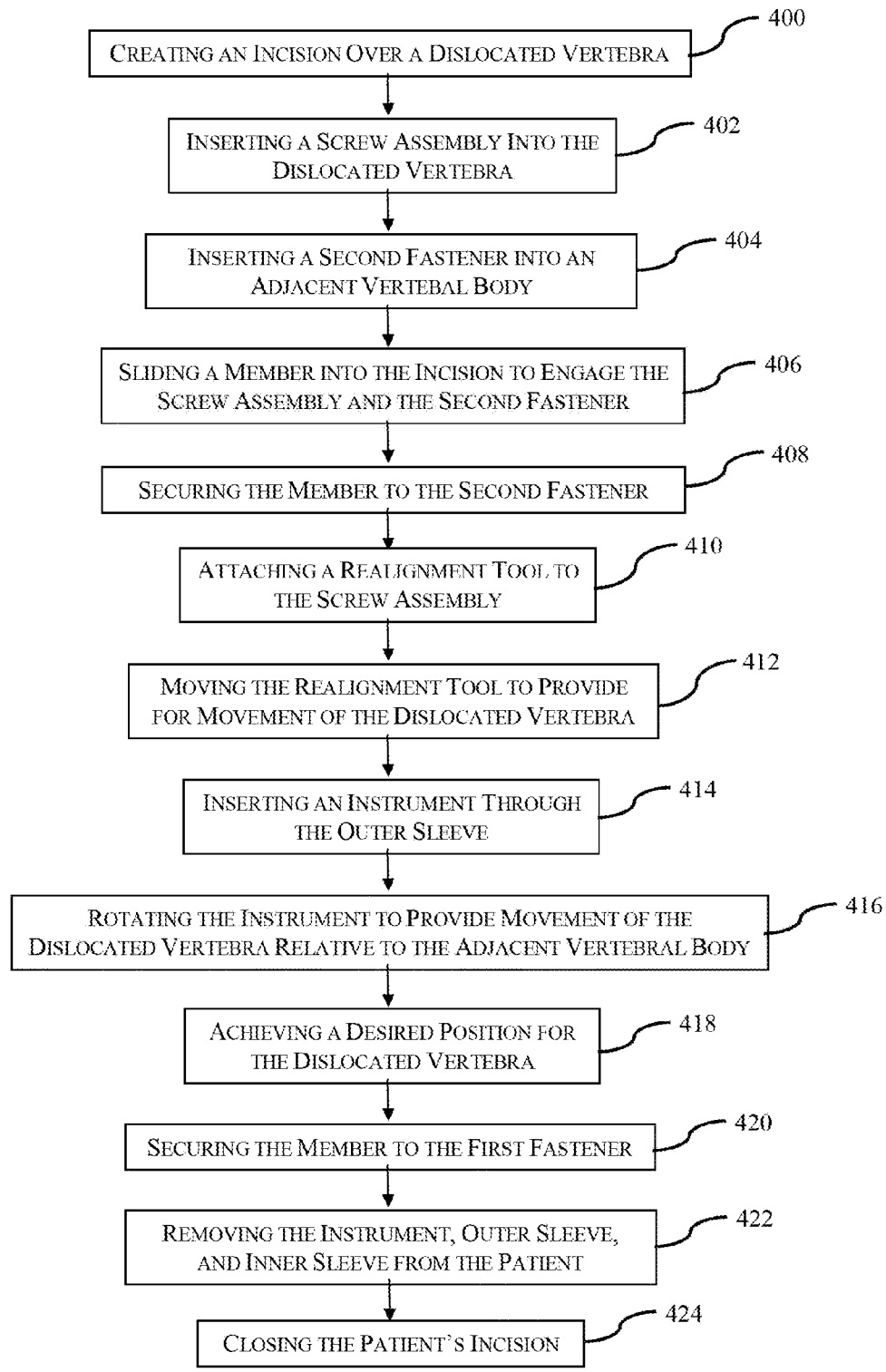
FIG. 13 depicts one embodiment of a method of using a realignment system, in accordance with an aspect of the present invention.

As shown in FIG. 9, the desired reduction and translation of the cephalad vertebral body 80 has been achieved to realign the vertebral body 80 in the patient's spine and the ratcheting bar 40 is secured to the fasteners 20 with set screws 86. The ratcheting bar 40, fasteners 20, and set screws 86 remain in the patient to hold the patient's spine in the desired alignment. The above method may also be performed on the contra-lateral side of the spinal column for additional stability. Finally the patient's incision may be closed. In one embodiment, as shown in FIG. 13, a method for using a realignment system in accordance with one or more aspects of the present invention may include, for instance: creating an incision in a patient over a dislocated vertebra 400; inserting a screw assembly into the dislocated vertebra 402; inserting a second fastener into an adjacent vertebral body 404; sliding a member into the incision to engage the screw assembly and the second fastener 406; securing the member to the second fastener 408; attaching a realignment tool to the screw assembly 410; moving the realignment tool to provide for movement of the dislocated vertebra in an anterior or posterior direction 412; inserting an instrument through the outer sleeve 414 wherein the instrument engages a plurality of slots on the member; rotating the instrument to provide movement of the dislocated vertebra relative to the adjacent vertebral body in an inferior-superior direction 416; achieving a desired anterior-posterior position and inferior-superior position for the dislocated vertebra 418; securing the member in the first fastener 420; removing the instrument, the outer sleeve, and the inner sleeve from the patient 422; and closing the patient's incision 424.

As the realignment system 10 allows for both reduction and translation using a minimally invasive surgical technique for correction of, for example, spondylolisthesis, the system 10 may also be used for correction of grade I-IV slips.

Figure 10:
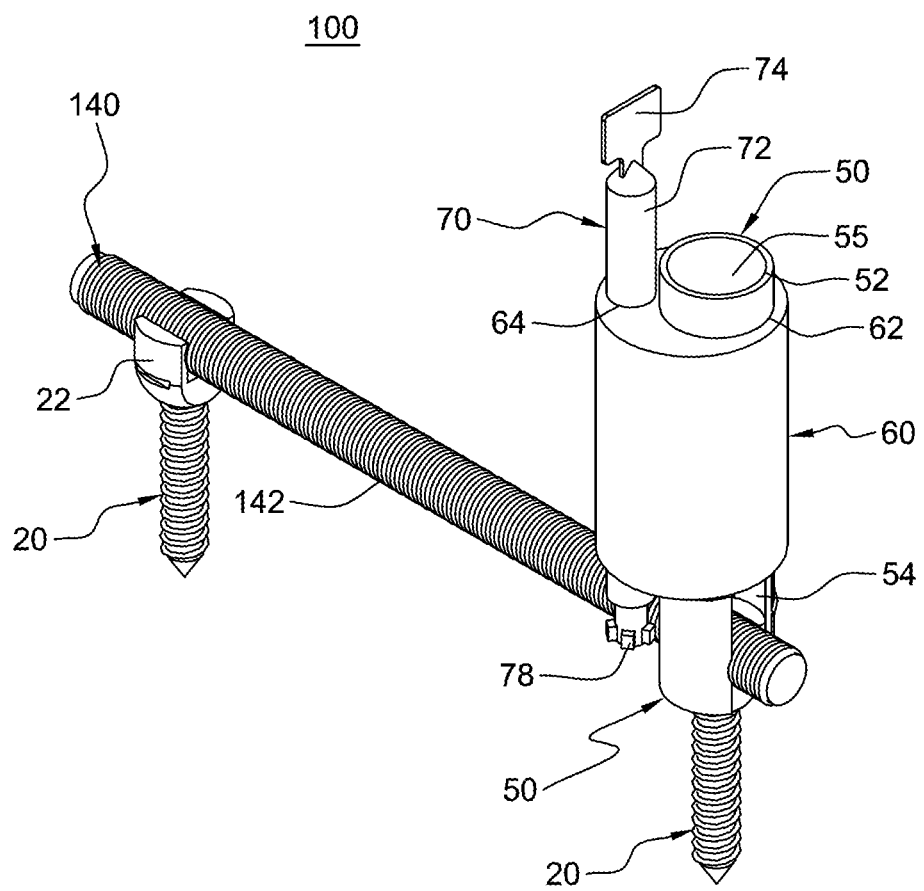
FIG. 10 is a perspective view of an embodiment of a minimally invasive realignment system, in accordance with an aspect of the present invention.

Another embodiment of a minimally invasive spinal column realignment system 100 is shown in FIG. 10. The system 100 may include at least two fasteners 20, a member 140, and an alignment assembly that may include an inner sleeve 50, an outer sleeve 60, and an instrument 70. The system 100 may also include at least two set screws or locking caps 86. The at least two fasteners 20, inner sleeve 50, outer sleeve 60, instrument 70, and set screws or locking caps 86 may be of the type described above with reference to the realignment system 10. The member 140 may have, for example, a generally circular, round or oval shape with, for example, a circle, round or oval cross-section and may include a plurality of circumferential flanges or slots 142 on an exterior surface of the member 140. The plurality of flanges or slots 142 of the member 140 are sized to mate with the protrusions 78 of the instrument head 76. Alternative configurations for the plurality of slots 142 on the member 140 are also contemplated, for example, the member 140 may contain a plurality of slots 142 only on the portion of the member 140 that mates with the instrument 70.

Figure 11:
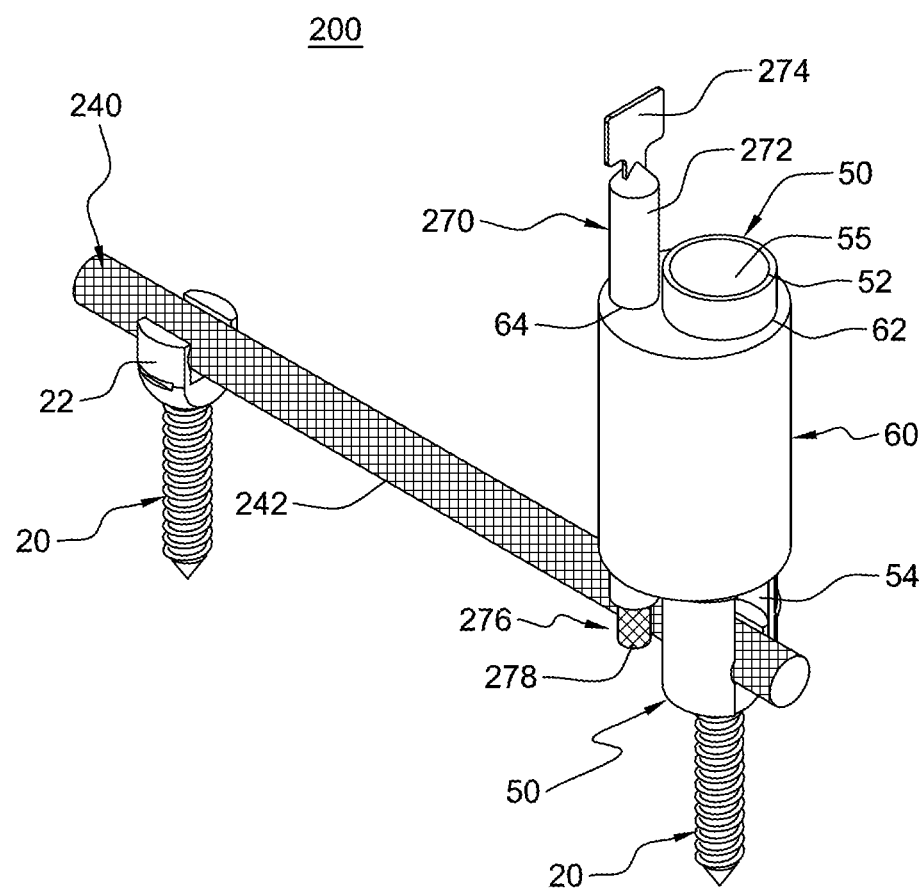
FIG. 11 is a perspective view of another embodiment of a minimally invasive realignment system, in accordance with an aspect of the present invention.

FIG. 11 shows yet another embodiment of a minimally invasive spinal column realignment system 200. The system 200 may include at least two fasteners 20, a member 240, and an alignment assembly that may include an inner sleeve 50, an outer sleeve 60, and an instrument 270. The system 200 may also include at least two set screws or locking caps 86. The at least two fasteners 20, inner sleeve 50, outer sleeve 60, and set screws or locking caps 86 may be of the type described above with reference to the realignment system 10. The member 240 may have, for example, a generally circular, round or oval shape with, for example, a circle, round or oval cross-section and may have an exterior surface that is knurled, grooved, or ridged 242. The instrument 270 may include a shaft 272 with a handle 274 at a first end and a head 276 at a second end. The head 276 may include a knurled, grooved, or ridged end 278. The knurled, grooved, or ridged exterior surface 242 of the member 240 is configured to mate with the knurled, grooved, or ridged end 278 of the instrument head 276. Alternative configurations for the exterior surface 242 on the member 240 are also contemplated, for example, the member 240 may contain a knurled, grooved, or ridged exterior surface 242 on only a portion of the member 240 that mates with the instrument 270.

Figure 12:
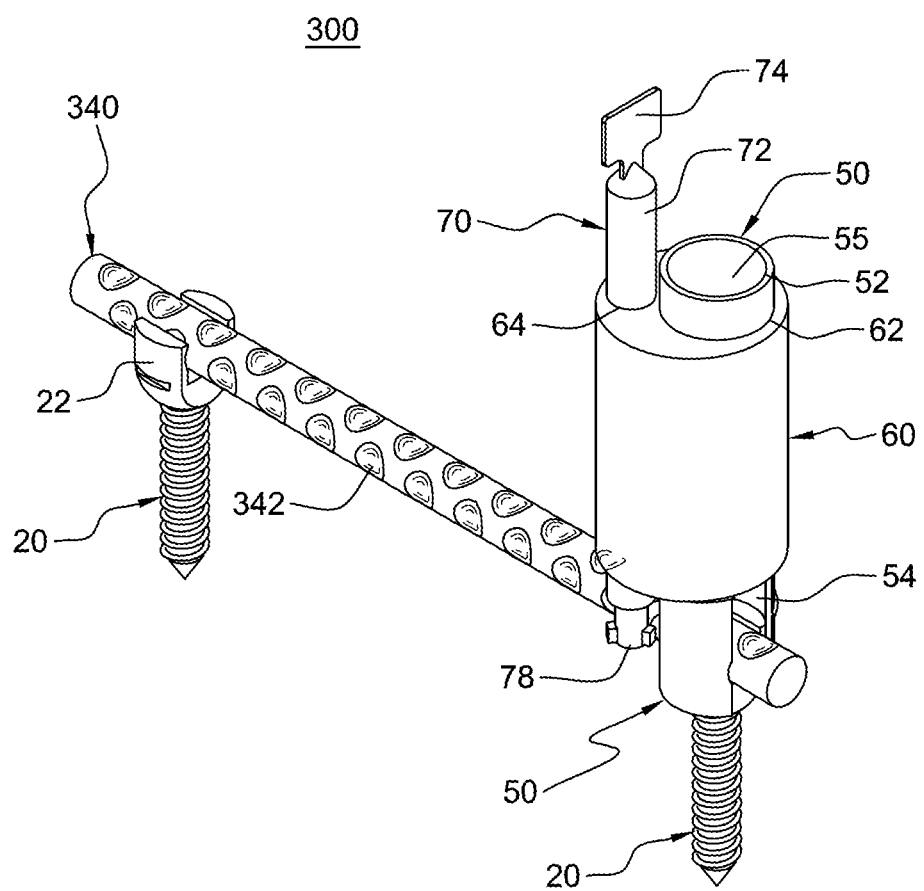
FIG. 12 is a perspective view of yet another embodiment of a minimally invasive realignment system, in accordance with an aspect of the present invention.

Another embodiment of a minimally invasive spinal column realignment system 300 is shown in FIG. 12. The system 300 may include at least two fasteners 20, a member 340, and an alignment assembly that may include an inner sleeve 50, an outer sleeve 60, and an instrument 70. The system 300 may also include at least two set screws or locking caps 86. The at least two fasteners 20, inner sleeve 50, outer sleeve 60, instrument 70, and set screws or locking caps 86 may be of the type described above with reference to the realignment system 10. The member 340 may have, for example, a generally circular, round or oval shape with, for example, a circle, round or oval cross-section and may have a plurality of grooves or indents 342. The plurality of grooves or indents 342 may be, for example, on a medial-lateral surface, an anterior-posterior surface, or as illustrated may be on both the medial-lateral surface and the anterior-posterior surface. As shown in FIG. 12, the grooves or indents 342 may be positioned such that the grooves 342 on the medial-lateral surfaces are offset from the grooves 342 on the anterior-posterior surfaces. The grooves or indents 342 of the member 340 are configured to mate with the protrusions 378 of the instrument head 76. Alternative configurations for the exterior surface 342 on the member 340 are also contemplated, for example, the member 340 may contain grooves or indents 342 only on the surface or portion of the member 340 that mates with the instrument 70.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A spinal column realignment system, comprising:
   at least two fasteners for insertion into two adjacent vertebral bodies of a patient, wherein the at least two fasteners each comprises a head and a threaded shank extending away from the head;

a member configured to engage the heads of the at least two fasteners, wherein the member comprises a plurality of indentations on at least one side;

an outer sleeve including a first lumen and a second lumen;

an inner sleeve for insertion through the first lumen of the outer sleeve to engage a first fastener of the at least two fasteners and the member; and an instrument configured for insertion through the second lumen and for engagement with the member;

wherein the plurality of indentations of the member engage a plurality of protrusions on a head of the instrument.

2. The system of claim 1, wherein the head includes an inner channel and at least one slot on an exterior surface.

3. The system of claim 2, wherein the inner sleeve has an opening configured to engage the first fastener.

4. The system of claim 3, wherein the opening includes at least one protrusion on an interior surface of the opening for engaging the at least one slot on the exterior surface of the head of the first fastener.

5. The system of claim 3, wherein the inner sleeve further comprises an opening at a first end of the inner sleeve and a lumen extending from the first end to a second end.

6. The system of claim 5, wherein the lumen is sized to allow a set screw be passed through for engagement with the head of the first fastener.

7. The system of claim 1, wherein the inner sleeve comprises an exterior thread disposed on an exterior surface for engaging a corresponding interior thread inside the first lumen of the outer sleeve.

8. The system of claim 7, wherein the plurality of indentations are a plurality of circumferential flanges on an exterior surface of the member to engage the plurality of protrusions on the head of the instrument.

9. The system of claim 1, wherein the member has a cross sectional shape selected from a square, a circle, an oval, and a polygonal.

10. The system of claim 1, wherein the instrument comprises:

a shaft with a first end and a second end;
a handle on the first end for rotating the instrument; and
a head on the second end, wherein the head comprises a plurality of protrusions for engaging the member.

11. The system of claim 10, wherein the plurality of indentations of the member are configured to receive the plurality of protrusions of the head to move the member relative to the two adjacent vertebral bodies.

12. The system of claim 1, further comprising:
a second outer sleeve including a first lumen; and
a second inner sleeve for insertion through the first lumen of the outer sleeve to engage a second fastener of the at least two fasteners and the member.

13. The system of claim 1, wherein the plurality of indentations extend along the entire length of the member.

14. The system of claim 1, wherein the member has a rectangular cross-sectional shape.

15. The system of claim 1, wherein the plurality of indentations are selected from a group consisting of a plurality of slots, a plurality of grooves, a plurality of indentations defined by a plurality of flanges, a plurality of indentations defined by a plurality of ridges, and a plurality of indentations defined by a plurality of knurls.

16. The system of claim 1, wherein the plurality of protrusions are positioned around a circumference of the head of the instrument.

17. A method of using a realignment system, comprising:
creating an incision in a patient over a dislocated vertebra;
inserting a screw assembly into the dislocated vertebra, wherein the screw assembly comprises a first fastener, an inner sleeve, and an outer sleeve;
inserting a second fastener into an adjacent vertebral body;
sliding a member into the incision to engage the screw assembly and the second fastener;
securing the member to the second fastener;
attaching a realignment tool to the screw assembly;
moving the realignment tool to provide for movement of the dislocated vertebra in an anterior or posterior direction;
inserting an instrument through the outer sleeve, wherein the instrument engages a plurality of slots on the member;
rotating the instrument to provide movement of the dislocated vertebra relative to the adjacent vertebral body in an inferior-superior direction;
achieving a desired anterior-posterior position and inferior-superior position for the dislocated vertebra;
securing the member to the first fastener;
removing the instrument, the outer sleeve, and the inner sleeve from the patient; and
closing the patient's incision.

18. The method of claim 17, wherein securing the member in the second fastener comprises inserting a first locking cap into a head of the second fastener and securing the member in the first fastener comprises inserting a second locking cap into a head of the first fastener.

19. The method of claim 17, wherein moving the realignment tool to provide for movement of the dislocated vertebra in an anterior-posterior direction and turning the instrument to provide movement of the dislocated vertebra relative to the adjacent vertebral body in an inferior-superior direction may be performed simultaneously.

20. The method of claim 17, wherein the adjacent vertebral body is a caudal vertebral body.

* * * * *